(12) United States Patent
Eliaz

(10) Patent No.: US 9,427,449 B2
(45) Date of Patent: Aug. 30, 2016

(54) BINDING OF GALECTIN-3 BY LOW MOLECULAR WEIGHT PECTIN

(75) Inventor: Isaac Eliaz, Sebastopol, CA (US)

(73) Assignee: ECONUGENICS, INC., Santa Rosa, CA (US)

( * ) Notice: Subject to any disclaimer, the term of this patent is extended or adjusted under 35 U.S.C. 154(b) by 300 days.

(21) Appl. No.: 13/153,648

(22) Filed: Jun. 6, 2011

(65) Prior Publication Data

US 2011/0294755 A1 Dec. 1, 2011

Related U.S. Application Data

(63) Continuation-in-part of application No. 11/485,955, filed on Jul. 14, 2006, now Pat. No. 8,426,567, and a continuation-in-part of application No. 12/984,843, filed on Jan. 5, 2011, now Pat. No. 8,916,541.

(60) Provisional application No. 60/711,415, filed on Aug. 26, 2005, provisional application No. 61/447,138, filed on Feb. 28, 2011.

(51) Int. Cl.

| A61K 31/715 | (2006.01) |
| A61K 31/732 | (2006.01) |
| C08B 37/00 | (2006.01) |
| A61K 31/734 | (2006.01) |

(52) U.S. Cl.
CPC .......... *A61K 31/734* (2013.01); *A61K 31/732* (2013.01)

(58) Field of Classification Search
CPC ......................... A61K 31/732; C08B 37/0045
USPC ....................................... 514/54; 536/2, 124
See application file for complete search history.

(56) References Cited

U.S. PATENT DOCUMENTS

| 6,274,566 B1 | 8/2001 | Eliaz et al. |
| 6,462,029 B1 | 10/2002 | Eliaz |
| 6,890,906 B2 * | 5/2005 | Chang et al. ............ 514/23 |
| 2007/0049551 A1 | 3/2007 | Eliaz |

FOREIGN PATENT DOCUMENTS

DE          10214005 A1 * 10/2003  ......... A23L 1/3008

OTHER PUBLICATIONS

Sethi, et al., "Biomarkers for the Diagnosis of Thyroid Cancer", J. Exp. Ther. Oncol., 2010, 8(4): 341-52, Abstract.
Psarras, et al., "Regulation of Adverse Remodelling by Osteopontin in a Genetic Heart Failure Model", Eur. Heart J. Apr. 26, 2011, Abstract.
Saegusa, et al., "Galectin-3 is Critical for the Development of the Allergic Inflammatory Response in a Mouse..", Am. J. Pathol. Mar. 2009; 174(3):922-31, Abstract.
Wang, et al., "Intra-Articular Lentivirus-Mediated Delivery of Galectin-3 shRNA and Galectin-1 Gene . . . " Gene. Ther. Oct. 2010;17(10):1225-33, Abstract.
Forsman, et al., "Galectin 3 Aggravates Joint Inflammation and Destruction in Antigen-Induced Arthritis", Arthritis Reheum. Feb. 2011;63(2):445-54, Abstract.
Canning, et al., "Inhibition of Advanced Glycation and Absence of Galectin3 Prevent Blood-Retinal.." Exp. Diabetes Res. 2007;2007:51837, Abstract.
Mensah-Brown, et al., "Targeted Disruption of the Galectin-3 Gene Results in Decreased . . . " Clin. Immunol. Jan. 2009;130(1):83-8, Abstract.
Breuilh, et al., "Galectin-3 Modulates Immune and Inflammtory Responses During Helminthic . . . ", Infect. Immun. Nov. 2007;75(11):5148-57, Abstract.
Ferraz, et al., "Lack of Galectin-3 Alters the BAlance of Innate Immune Cytokines and Confers . . . ", Eur. J. Immunol. Oct. 2008;38(10):2762-75, Abstract.
Vankrunkelsven, et al., "Lack of Galectin-3 Alleviates TrypanosomiasisAssociated Anemia . . . ", Immunobiology. Sep.-Oct. 2010;215(9-10):833-41, Abstract.
Yu, et al., "Galectin-3 Interaction with Thomsen-Friedenreich Disaccharide on Cancer-Associated . . . " The Journal of Biological Chemistry, vol. 282, No. 1, pp. 773-781., Jan. 5, 2007.
Meltser, et al., "c-Abl Downregulates the Slow Phase of Double-Strand Break Repair", Cell Death and Disease (2010).
U.S. Appl. No. 60/711,415, filed Aug. 26, 2005, Eliaz.
U.S. Appl. No. 12/984,843, filed Jan. 5, 2011, Eliaz.
U.S. Appl. No. 61/447,138, filed Feb. 28, 2011, Eliaz.
De Boer, et al., "Galectin-3: A Novel Mediator of Heart Failure Development and Progression", Eur. J. Heart Fail. Sep. 2009;11(9):811-7, Abstract.
De Boer, et al., "Predictive Value of Plasma Galectin-3 Levels in Heart Failure with Reduced . . . " Ann. Med. Feb. 2011;43(1)60-8, Abstract.
Weigert et al., "Serum Galectin-3 is Elevated in Obesity and Negativey Correlates with Glycosylated . . . " J. Clin. Endocrinol Metab, Mar. 2010, 95(3):1404-1411.
Kolatsi-Joannou, et al., "Modified Citrus Pectin Reduces Galectin-3 Expression and Disease Severity . . . " PLOSONE, Apr. 2011, vol. 6, Issue 4.
Defillppi, et al., "Galectin-3 in Heart Failure—Linking Fibrosis, Remodeling, and Progression", U.S. Cardiology, vol. 7, Issue 1, 2010.
Lok, et al., "Prognostic Valu eof Galectin-3, a NOvel Marker of Fibrosis, in Patients with Chronic Heart Failure . . . ", Clin. Res. Cardiol (2010) 99:323-328.
Wang, et al., "Regulation of Prostate Cancer Progression by Galectin-3", The American Journal of Pathology, Apr. 2009, vol. 174, No. 4.
Zhao, et al., "Circulating Galectin-3 Promotes Metastasis by Modifying MUC1 Localization on Cancer . . . " Cancer Res. 2009; 69:(17), Sep. 1, 2009.
Zhao, et al., "Interaction Between Circulating Galectin-3 and Cancer-Associated Associated MUC1 Enhances Tumor . . . " Molecular Cancer 2010, 9:154.

(Continued)

*Primary Examiner* — Patrick Lewis
*Assistant Examiner* — Everett White
(74) *Attorney, Agent, or Firm* — Steven B. Kelber

(57) ABSTRACT

Administration of low molecular weight (10,000-20,000 Daltons, or lower) pectins, particularly modified citrus pectins (MCP), like PectaSol-C reduces galectins-3 levels in vivo. Reduction of galectin-3 levels by MCP inhibits inflammation, inhibits fibrosis formation in organs and tissues, and inhibits cancer formation, progression, transformation and metastases. The reduction in circulating, serum and cellular galectin-3, inherently resulting from the administration of MCP, provides benefit over a spectrum of biological conditions, as evidenced by in vivo trials.

2 Claims, No Drawings

(56) References Cited

OTHER PUBLICATIONS

Zuberi, et al., "Critical Role for Galectin-3 in Airway Inflammation and Bronchial Hyperresponsiveness . . . ", Am. J. Pathol. Dec. 2004;165(6):2045-53, Abstract.

Li, et al., "CD133(+) Human Pulmonary Adenocarcinoma Cells Induce Apoptosis of CD8(+) T-Cells . . . " Clin. Invest. Med. Feb. 1, 2010;33(1):E44-53, Abstract.

Liu, et al., "Inhibitory Effect of Modified Citrus Pectin on Liver Metastases in a Mouse Colon Cancer . . . ", World J. Gastroenterol. Dec. 28, 2008;14(48):7386-91, Abstract.

Federici, et al., "Galectin-3 Ablation Protects Mice from Diet-INduced NASH: A Major Scavenging Role . . . " J. Hepatol. May 2011;54(5):975-83, Abstract.

Honsawek, et al., "Elevation of Serum Galectin-3 and Liver Stiffness Measured by Transient Elastography . . . " Eur. J. Pediatr Surg. Apr. 12, 2011, Abstract.

Fowler, et al, "Galectin-3 Binds to Helicobacter Pylori O-Antigen: It Is Upregulated and Rapidly Secreted . . . " Cell Microbiol. Jan. 2006;8(1):44-54, Abstract.

Kim, et al., "Galectin-3 INcreases Gastric Cancer Cell Motility by Up-Regulating Fascin-1 Expression", Gastroenterology. Mar. 2010; 138(3):1035-45, Abstract.

Srikanta, et al., "Alterations of Matrix Metalloproteinases, Gastric Mucin and Prostaglandin E(2) . . . " Biochimie. Feb. 2010;92(2):194-203, Abstract.

Chiu, et al., "Diagnostic Utility of Galectin-3 in Thyroid Cancer", Am. J. Pathol. May 2010;176(5):2067-81, Abstract.

\* cited by examiner

BINDING OF GALECTIN-3 BY LOW MOLECULAR WEIGHT PECTIN

PRIORITY DATA AND INCORPORATION BY REFERENCE

This application is a continuation-in-part of U.S. Patent Application Ser. No. 11/485,955, filed Jul. 14, 2006, pending, which claims the benefit under 35 U.S.C. §119(e) of U.S. Provisional Patent Application Ser. No. 60/711,415, filed on Aug. 26, 2005, both of which are incorporated by reference herein in their entirety. This application is a continuation-in-part and also claims benefit of priority to U.S. patent application Ser. No. 12/984,843, filed Jan. 5, 2011, pending, and U.S. Provisional Patent Application Ser. No. 61/447,138 filed Feb. 28, 2011 both of which are incorporated by reference in their entirety. The above Amendment does not add new matter, clarifies prosecution and conforms this case to the submissions made in the original filing. Entry is respectfully requested.

BACKGROUND OF THE INVENTION

1. Field of the Invention

The present invention relates to improvement of mammalian, including human, biological conditions impacted by, or mediated by, galectin-3. Galectin-3 is a member of the lectin family, of which at least fourteen (14) mammalian galectins have been identified. Galectin-3 is approximately 30 kDa and, like all galectins, contains a carbohydrate-recognition-binding domain (CRD) of about one hundred thirty (130) amino acids that enable the specific binding of β-galactosides. Galectin-3 is encoded by a single gene, LGALS3, located on chromosome 14, locus q21-q22. It is expressed in the nucleus, cytoplasm, mitochondrion, cell surface, and extracellular space, and can circulate in the blood stream. This protein has been shown to be involved in a large number of biological processes, including cell adhesion, cell migration, cell invasion, cell activation and chemoattraction, cell growth and differentiation, cell cycle, and apoptosis. Given galectin-3's broad biological functionality, it has been demonstrated to be involved in a large number of disease states or medical implications. Studies have also shown that the expression of galectin-3 is implicated in a variety of processes associated with heart failure, including myofibroblast proliferation, fibrogenesis, tissue repair, inflammation, and ventricular and tissue remodeling. Elevated levels of galectin-3 in the blood have been found to be significantly associated with higher risk of death in both acute decompensated heart failure and chronic heart failure populations, as well as constituting a biomarker of cancer progression to a metastatic stage.

BACKGROUND OF THE INVENTION

In 2006, U.S. patent application Ser. No. 11/485,955 was filed, a utility patent application claiming priority from a 2005 provisional application. This patent application, making reference to earlier disclosures of administration of modified alginates and pectins, such as those in U.S. Pat. Nos. 6,274,566 and 6,462,029, disclosed for the first time the utility of using very specific low molecular weight pectins, such as PectaSol-C MCP available from EcoNugenics of Santa Rosa, Calif. This modified citrus pectin (MCP) and similar very low molecular weight pectins (molecular weight of 20,000 Daltons or less, preferably about 10,000 Daltons) is shown in U.S. patent application Ser. No. 11/485,955 to be effective in stimulating a variety of immune responses in mammals.

In the years since the filing which first set forth the administration of these low molecular weight modified citrus pectins, and similar pectins, research has demonstrated that at least one mode of action of MCP is the binding of galectin-3 molecules. This binding, an inherent feature of the inventions disclosed in U.S. patent application Ser. No. 11/485,955, is also a central mode of action in the later-filed U.S. patent application Ser. No. 12/984,843, filed Jan. 5, 2011 directed to the inhibition of certain cancers. In fact, it is now clear that administering PectaSol-C MCP or other low molecular weight pectins at the dosage levels of 5-1,500 mg/kg of body weight per day, with a preferred range of 10 mg/kg/day to 1,000 mg/kg/day inherently binds galectin-3 molecules in mammals in need of same in a variety of biological systems, providing therapeutic benefit against many of the disease conditions mentioned.

Thus, the activity of galectin-3 in aggravating or promoting cancer, as well as the ability of a cancer to metastasize, is widely commented on in the literature following the 2006 disclosure of the effectiveness of low molecular weight pectins like PectaSol-C in promoting immune systems. These literature findings stress repeatedly the importance of binding or reducing the circulating concentration or titer of galectin-3, and/or inactivating galectin-3 through galectin-3 binders such as PectaSol-C. See, for example, Wang et al, *Cell Death and Disease*, 1-10 (2010) (galectin-3 inhibition promotes treatment) and Yu et al, *J. Biol. Chemistry*, Vol. 282, 1, pp. 773-781 (2007) establishing that galectin-3 interactions may enhance formation of cancer or transformation of metastatic cancer.

Similar reports link acceleration of cancer formation and transformation to circulating galectin-3 concentrations, and suggest that reducing galectin-3 circulating concentrations, reducing its free expression or otherwise reducing available galectin-3 or galectin-3 interactions improve cancer prognosis. Zhao et al, *Cancer Res.* 69, 6799-6806 (2009), Zhao et al, *Molecular Cancer* 9, 154, 1-12 (2010) and Wang et al, *Am. J. of Pathology*, 174, 4, 1515-1523 (2009) wherein siRNA-induced reduction of galectin-3 is shown to slow the course of prostate cancer. Clearly, there is substantial literature that supports the conclusion that reducing circulating galectin-3, either by blocking its expression, or by binding it, as inherently disclosed in the 2006 filing of U.S. patent application Ser. No. 11/485,955, is important in controlling cancer.

Circulating galectin-3 is implicated in a wide variety of biological conditions, however. Cardiac fibrosis is gaining significant attention as a complicating risk factor in cardiac disease, and in particular, chronic heart failure (CHF). Lok et al, *Clin. Res. Cardiol*, 99, 323-328 (2010). DeFillipi et al, *U.S. Cardiology*, 7,1, 3-6 (2010) clearly indicate that circulating galectin-3 is an important factor in fibrosis of many organs and organ systems, and that reducing circulating galectin-3 may have an important role in remediating cardiac injury and progression to heart failure (HF). Similarly, Psarras et al, *Eur. Heart J.*, Apr. 26, 2011 demonstrate that reduction in galectin-3 levels in the myocardium may reduce fibrosis in the heart and improve outlook. De Boer et al, *Ann. Med.*, 43,1, 60-68 (2011) identify galectin-3 as a key indicator in cardiac health. Shash et al, *Eur J. Heart Fail.*, 12, 8, 826-32 (2011) identify galectin-3 levels as a key agent in heart failure through fibrosis. De Boer et al. *Eur. J. Heart Fail.*, 11, 9, 811-817 (2009) link an increase in galectin-3 expression and presence to heightened fibrosis, and heart failure. The same article links galectin-3 to inflammation. Inflammation is the hallmark of arteriosclerosis and therefore galectin-3 levels also contribute to coronary artery disease, peripheral artery disease, strokes, and vascular dementia.

Fibrosis and inflammation, both mediated to some degree by galectin-3 (cellular or circulating) are implicated in a variety of conditions of the mammalian body, not just cardiac injury and heart failure. The binding of galectin-3 achieved by administration of low molecular weight pectins (at least, as reflected in U.S. patent application Ser. No. 11/485,955 10,000 -20,000 Daltons molecular weight such as PectaSol MCP) is effective in reducing trauma due to kidney injury. Kolatsi-Jannou et al, *PlusOne*, 6, 4, e18683 (2011). The reduction in circulating galectin-3 levels is also indicated to reduce inflammation associated with type 2 diabetics, and similar metabolic diseases. Weigert et al, *J. Endocrinol. Metab.* 95, 3, 1404-1411 (2010). Thus, high levels of galectin-3 have been linked to thyroid cancer, Sethi et al, *J. Exp. Ther. Oncol.*, 8, 4, 341-52 (2010) and reduction of galectin-3 expression and circulation may delay or reduce tumor cell transformation. Chiu et al, *Am J. Pathol.* 176, 5, 2067-81 (2010).

As noted, galectin-3 is implicated in a wide variety of biological conditions, and a reduction in galectin-3 activity, such as that which can be achieved by galectin-3 binding with PectaSol-C MCP and similar low molecular weight pectins may be of value in treating gastric ulcerative conditions. Srikanta, *Biochimie*, 92, 2, 194-203 (2010). Kim et al, *Gastroenterology*, 138, 1035-45 (2010) indicate that reducing galectin-3 levels may be of therapeutic value in reducing gastric cancer progression. By the same methodology, reducing galectin-3 levels sensitizes gastric cancer cells to conventional chemotherapeutic agents. Cheong et al, *Cancer Sci.*, 101, 1, 94-102 (2010). Galectin-3 is implicated in a wide variety of gastrointestinal conditions. Reducing galectin-3, by binding for example, may reduce inflammation in the gut mucosa, making MCP an important agent for treatment of ulcerative colitis, non-specific colitis and ileitis, Crohn's disease, Celiac disease, and gluten sensitivity. Fowler et al, *Cell Microbiol.*, 81, 1, 44-54 (2006).

Biliary artesia, a liver disease, is associated with extensive fibrosis of the liver linked with elevated galectin-3 levels. Honsawek et al, *Eur. J. Pediatr. Surg., April,* 2011. Reduction of galectin-3 levels resulted in a general improvement in hepatic health, including reducing inflammation, hepatocyte injury and fibrosis. Federici et al, *J. Heptal.*, 54, 5, 975-83 (2011). See also, Liu et al, *World J. Gastroenterol.* 14, 48, 7386-91 (2008) which reported, following Applicant's teaching in 2005 and 2006 to administer low molecular weight MCP, that MCP inhibited liver metastases of colon cancer and reduced galectin-3 concentrations. MCP may be used for prevention of liver inflammation, liver fibrosis and liver cirrhosis as well as post-disease liver damage, including the various viral hepatitis disease (B, C, and others) and may be used as well in the treatment of parasitic and chemical hepatitis, chemical liver damage, and others.

SUMMARY OF THE INVENTION

The invention lies in the recognition that the method described in U.S. patent application Ser. No. 11/485,955 of administering low molecular weight pectins, such as modified citrus pectin, having a molecular weight of between 10,000-20,000 Daltons, in a therapeutically effective dosage, has implications far beyond stimulating the immune system. Because this administration, particularly oral or intravenous, inherently binds cellular, serum and circulating galectin-3, it is implicated in a wide variety of biological conditions and may be effective in ameliorating a wide variety of disease states and conditions.

Further improvement can be obtained in selecting the MCP to have a molecular weight of between 3,000-13,000 Daltons that is mostly linear homogalacturonan with fewer than ten percent (10%) esterification, and maintaining a percentage of rhamnogalacturonan-I, II in the MCP to approximately ten percent (10%), while reducing the amount of mono galacturonic acid to under ten percent (10%). The reduction in molecular weight promotes bioavailability (absorption into the circulatory system from the gastrointestinal tract), the degree of esterification (bulky side groups which contribute to cross bridging between pectin fibers) decreased below ten percent (10%) in the MCP contributes to the galectin-3 binding by fostering open fibers, allowing increased accessibility to binding galectin-3, while the reduction in mono-galacturonic acid (representative of inactive total breakdown of the pectin fiber into its major single subunit) increases that amount of MCP available for effectively binding galcetin-3. Therapeutic properties in vivo are further improved by selecting a modified citrus pectin with approximately ten percent (10%) rhamnogalcturonan-I, II content. Pectic rhamnogalacturonan-1 has been shown to induce apoptosis in melanoma cells by interacting with Gal-3. Rhamnogalacturonan-II has demonstrated a strong binding potential for heavy metal chelation. The modified citrus pectin, prepared by enzymatic degradation, results in shorter chain molecules of low esterification with enhanced bio-availability and binding potential to galectin-3.

This modified citrus pectin can be used to improve or enhance a mammal's immune reaction, as disclosed in U.S. patent application Ser. Number 11/485,955. The power of binding galectin-3, a ubiquitous molecule, without eliminating it from circulation, is powerful beyond this limited indication, however. Galectin-3 is implicated, as noted, in a wide variety of medical conditions. The inhibition of the growth and transformation of various cancers, the inhibition of fibrosis in a variety of organs and organ systems, the reduction in inflammation associated with galectin-3, all combine to provide a powerful method of treatment in a wide variety of situations. The issue is more of patient selection than treatment modification. In 2006, Applicant taught that MCP should be administered in a range of low molecular weight pectins at the dosage levels of 5-1,500 mg/kg of body weight per day, with a preferred range of 10 mg/kg/day to 1,000 mg/kg/day to achieve the desired results. This range inherently achieves binding or inactivation of cellular, serum and circulating MCP. Particularly for conditions characterized at least in part by fibrosis, a reduced preferred range of 10 mg/kg/day-750 mg/kg/day may provide even better effects.

PectaSol-C is only one modified pectin useful in this invention. In general, pectins of reduced molecular weight (10,000 to 20,000 Daltons or lower) having a lower percentage of mono galacturonic acid and having approximately ten percent (10%) rhamnogalcturonan-I, II all exhibit a higher rate of forming complexes with the multifunctional carbohydrate-binding protein, galectin-3, and thus reducing the effective level of galectin-3 to which a body, injured organs and threatened cells are exposed. In addition to the available commercial sources of low molecular weight pectins, their preparation is discussed in detail, Pienta et al, *J. Nat'l. Cancer Inst.,* 87, 348-352 (1995). In an alternative embodiment, low molecular weight pectin can also be synthesized. Specific molecular structures such as, for example, polygalacturonic acid, side branches and neutral sugars in the desired range as specified above can be synthesized to create a more consistent, accurate and highly reproducible molecular weight. By synthesizing MCP, an optimal structure within the molecular weight range of 10-20 KD, and more preferably 3-13 KD can be produced. Whether derived from reduced natural starting materials, or synthesized, administration of these lower molecular weight pectins, 20,000-10,000 Daltons, or even lower, 13,000-3,000 Daltons, is a preferred method of practicing the invention.

DETAILED DESCRIPTION OF THE INVENTION

The binding of galectin-3 by MCP is an event that will aid medical conditions over a wide variety of indications. These include cancer, inflammation and fibrosis, heart disease, kidney damage, liver damage, bladder disease, thyroid disease, pulmonary disease, immune response, stroke, persistent acute inflammation due to non-degradable pathogens, persistent foreign bodies, or autoimmune reactions, hypersensitivities and allergies, pesticides, environmental toxins, and heavy metals, as well as heterogenic conditions such as radiation (examples being medical procedures such as various radiation therapies, exposure to ionizing radiation, nuclear radiation, cosmic radiation, electromagnetic radiation) and chemotherapy damage, and post radiation and chemotherapy induced inflammation and fibrosis. As noted above, elevated galectin-3 levels are associated with (1) growth, transformation and metastatic migration of cancer cells across a wide variety of cancers, including liver, breast, prostate, colon, thyroid, gallbladder, nasopharyngeal, lymphocytic leukemia, melanoma and lung cancers among others, as well as reducing sensitivity in these cancers to conventional antineoplastic agents; (2) development and extension of fibroses beyond normal and healthy levels, in situations associated with cardiovascular disease and heart failure, in tissue injury including brain, lungs, renal, hepatic, heart and gastroenterologic situations as well as tissue damage due to radiation and chemotherapy exposure and persistent acute inflammation due to non-degradable pathogens, persistent foreign bodies, or autoimmune reactions, hypersensitivities and allergies; and (3) in inflammation that may be associated with disease or organ failure modes, including diabetes (I and II), heart disease and dysfunction, atherosclerosis, asthma (bronchial inflammation), ulcers, intestinal inflammation in the bowels (inflammatory bowel diseases), hepatic inflammation associated with both alcohol and non-alcohol related cirrhosis and inflammation, liver infections such as viral hepatitis among others. Other indications associated with inflammation and susceptible to treatment by administration of MCP include parasite-induced conditions, such as trypanosomiasis, cerebral malaria, and inflammation and resistance to various infections including *Paracoccidiosis brasiliensis* (fungal infection), schistosomiasis, granulatomatous bronchopneumonia, and in inflammation associated with arthritis and other diseases of the skeletomuscular and skin systems, including inflammation and fibrosis related conditions such as psoriasis and aging of the skin.

Reference is made herein to the binding of galectin-3 by MPC of the invention. Binding occurs between the two molecules in in vitro assays and there is a natural chemical bond possible between the reactive moieties of the two compounds. In vitro assays rarely reflect, at a microscopic and chemical level, the actual mechanisms that occur in vivo. Binding of galectin-3 by MCP in vivo is an event that may be reversible to some degree—in the same fashion that an antibody may bind and then release a poorly held antigen. Galectin-3 is ubiquitous in mammals, found in many different tissues and spaces. Administration of MCP does not appear to result in removal of all galectin-3 from the body. By the term binding, Applicant intends to describe the formation of a complex between galectin-3 and MCP that removes the galectin-3 from active involvement in the metabolic and biological processes of the body. Whether that complex is permanent and eliminated from the body over time, or reversible, does not appear to impact the relief obtained.

It is to be understood that MCP rarely mediates only inhibition of cancer progression, fibrosis or inflammation. These are conditions that are closely related, and tumor growth is frequently combined with inflammation and development of fibroses. Inflammation enhances the speed with which a cancer progresses, so treatment of one may include treatment of the other. Certainly, non-cancerous diseases, particularly heart disease and atherosclerosis, arthritis and diabetes are associated with inflammation and fibrosis. There will be patients in need of treatment primarily for inhibition of inflammation, patients in need of treatment primarily for suppression of fibrosis, and patients whose primary indication is the progression or transformation of cancer. While patient selection is a critical step in the methods embraced by this invention, it does not alter the fact that the patients receiving MCP in amounts of 5-1,500 mg/kg/day will receive the full benefit of MCP, independent of their primary indication.

The MCP of this invention may be the MCP of 10,000-20,000 Daltons, with a degree of etherification of less than about ten percent (10%). Further research has demonstrated that even lower molecular weight MCP may be more efficacious, identifying a preferred range of 3,000-13,000 Daltons molecular weight. With this newer formulation has come a small revision in the preferred range of administration. While 5-1,500 mg/kg/day remains an effective range, more effective MCP may be administered in a more preferred range of 10 mg/kg/day to 750 mg/kg/day. The MCPs of this invention may be administered over a prolonged period of time, as many disease conditions associated with inflammation and fibrotic complications are chronic in nature. Extended administration of MCP has not shown toxicity or presented issues of tolerance in any way. No cytopathic or toxicologic complications are associated with the administration of MCP in this range either orally or intravenously. These MCP are readily absorbed intrabucally or through the intestinal mucosa into the bloodstream. In one alternative embodiment, the MCP may be encapsulated, as a powder, into gelatin capsules which may, for example, include 500-800 mg/capsule. Alternatively, a water-based preparation may be used, for example, six (6) capsules taken three (3) times a day with a full eight (8) ounces of water or juice. Controlled dosage formulations are preferred to ensure adequate, constant dosage over time.

MCPs may be combined with a wide variety of pharmaceutically acceptable carriers, conventional excipients, flavorings and the like that are suitable for oral or intravenous administration, depending on the protocol desired. The modified pectins may also be administered together with agents that will enhance complexation with galectin-3, such as glutathione-rich why protein and other binding adjuvants. Chelating agents, such as 2,3 dimercapto-1-propane sulphonic acid and DL-2,3-dimercapto-succinic acid, EDTA may also be useful. MCP can be added to formulations that include pharmaceuticals, botanicals, mineral and vitamins, to create additional effects, as needed. Absorption may be enhanced by using intrabuccal and transdermal delivery systems.

It should be noted that commonly, inflammation and fibrosis can be induced by human agency, not just trauma or disease condition. The administration of MCP and its binding of galectin-3 can be effective in reducing or preventing organ damage induced by chemotherapy and other pharmaceuticals. Some examples include bleomycin, which induces lung fibroses, and a wide variety of cardiac drugs such as amiodarone. Adriamycin and doxorubicin are widely prescribed and present cardiac inflammation and fibroses issues. *Bacillus* Calmette-Guerin washes to treat bladder cancer induce systemic inflammation and cyclophosphamide also induces bladder damage. Ciclosporine, a widely used immunosuppressant drug, and the active agent in Restasis™, induces kidney toxicity and inflammation. Studies indicate that the vast array of organ damage caused by prescribed pharmaceuticals is mediated, at least in part, by elevated galectin-3 levels, and can be limited if not eliminated by administration of MCP.

EXAMPLES

Renal Injury

Renal insult is simulated in mice with folic acid. Folic acid induced renal injury candidates were pretreated with either water, or water supplemented with one percent (1%) Pecta-Sol-C one (1) week before injection of folic acid. The gross changes associated with the renal insult, including enlarged kidneys and weight loss, were reduced in mice receiving MCP. In the recovery phase, MCP-receiving mice demonstrated reduced galectin-3 and decreased renal fibrosis, macrophages, pro-inflammatory cytokine expression and apoptosis. The levels of other renal-associated galectins, including galectin-1 and galectin-9, were unchanged. Clearly, MCP was of value in suppressing both inflammation and fibrosis relative to organ injury. Kolatsi-Joannou, *PLoS One,* 8, 6 (4), e18683 (2011).

Thyroid Cancer Treatment

Patients with papillary thyroid cancer were administered a galectin-3 binding molecule, inhibiting galectin-3 concentrations in the patients so studied. Patients with reduced galectin-3 concentrations exhibited improved apoptotic activity, and improved sensitivity to both radiation and chemotherapeutic treatment (doxorubicin). Galectin-3 inhibition by administration of a molecule that binds to galectin-3 offers a promising therapeutic treatment to both inhibit cancer, and elevate the utility of conventional antineoplastic agents and treatments. Mol. Cancer Res., 7, 10, 1655-62 (2009).

Lung Cancer Treatment

In patients with pulmonary adenocarcinoma, the test group was administered polyclonal antibodies which bind galectin-3 in much the same fashion as MCP does. The tissues of these patients exhibited a significant inhibition of cancer cell growth, the galectin-3 clearly playing a role in oncogenesis. Binding of galectin-3, as a means of reducing its effective local concentration, whether by antibody or MCP offers a therapeutic target for cancer intervention. Li et al, *Clin. Invest. Med.,* 33, 1, e44-53 (2010).

Asthma And related Inflammation

Mice with reduced galectin-3 concentrations were compared with mice with normal galectin-3 levels in mice with induced asthma (ovalbumin induced). Mice with lower levels of galectin-3 exhibited fewer eosinophils and lower goblet metaplasia, less airway hyperressponsiveness and a different Th1/Th2 response. Administration of MCP is an effective means of reducing the concentration of galectin-3 to which cells, organs and systems sensitive to inflammation are exposed. This reduction provides benefits in treatment to intractable disease states. Zuberi et al, *Am J. Pathol.* 165, 6, 2045-53 (2004).

Inflammation of the Gastrointestinal Tract

Inflammation is a normal mammalian response to cellular stress in a wide variety of environments. In gastric ulcers, inflammation can often represent an imbalance in mucosal defense. Wistar albino rats with induced gastric ulcers with a 3-fold reduction in galectin-3 concentration exhibited improved protection against inflammation and gastric wall damage. Galectin-3 is, generally, an inflammation modulator, and wherever that inflammation is a response to a condition that is injurious or imbalanced, MCP may be administered to reduce galectin-3 concentration locally and inhibit associated inflammation. Srikanta et al, *Biochimie,* 92, 2, 194-203 (2010).

Inflammation And Fibrosis of the Liver

Normal mice and galectin-3 deficient mice were compared after being fed a diet that results in the formation of advanced lipoxidation endproducts or ALEs associated with inflammation and fibrosis. Galectin-3 deficient mice exhibited significantly reduced hepatic inflammation and fibrosis together with reduced hepatocyte injury. Reduced concentration of galectin-3 may also lead to reduced insulin resistance. MCP reduces effective concentration of galectin-3 in tissues threatened by inflammation and fibrosis. Reducing galectin-3 concentration may be an effective therapeutic measure in addressing liver disease. Federici, *J. Hepatol.* 54, 5, 975-83 (2011).

Treatment of Liver Cancer

Balb/C mice were divided into a control group, and test groups that received varying levels of MCP following administration of colon cancer cells to the spleen to set up a colon cancer liver metastasis model. The MCP was delivered in varying levels through the drinking water. The concentration of serum galectin-3 was significantly higher in the control group. Expression of galectin-3 was found to significantly increase liver metastases of colon cancer. The administration of MCP to reduce the concentration of galectin-3 resulted in a significant reduction in liver metastases that varied directly with the concentration of MCP in the drinking water (the higher the concentration, the more dramatic the reduction in liver metastases.) Liu et al, *World J. Gastroenterol.* 14, 48, 7386-91 (2008).

Inflammation To Due Parasite Invasion

In mammals infected with Trypanosoma brucei, chronic inflammation is a key factor in the development of ACD. In mice with a reduced galectin-3 concentration, significantly lower levels of anemia during infection were observed, and the mice survived twice as long as untreated mice. The mice with a reduced galectin-3 concentration reflected reduced liver pathology as well. Reduced inflammation was accompanied by reduced anemia and better survival, indicating reduction of galectin-3 levels is a potential therapeutic avenue for liver malfunction. MCP may be administered to reduce effective galectin-3 levels. Vankrunkelsven, *Immunobiology,* 215, 9-10, 833-841 (2010). In a related study, galectin-3 deficient mice demonstrated lower bacterial count when challenged with a sublethal dose of *Rhodococcus equi,* together with a decreased frequency of bacterial replication and survival. Ferraz et al, *Eur. J. Immunol.* 38, 10, 2762-75 (2008). Reduced levels of galectin-3 in mice were also associated with reduced inflammation in mice infected with *Schistosoma mansoni.* Breuilh et al, *Infect. Immun.* 75, 11, 5148-57 (2007).

Diabetes Resistance

Mice were exposed to conditions that induce hyperglycemia and similar diabetic traits. In mice with reduced galectin-3 levels, measurements of glycemia, quantitative histology and insulin content showed these mice to be resistant to the development of diabetes, as compared with mice with normal levels of galectin-3. The same mice showed a reduction in inflammation. One method of reducing the galectin-3 levels to which challenged tissues and organs are exposed is by systemic administration of MCP, orally or intravenously.

Reduction in galectin-3 levels is associated with resistance to diabetogenesis. Mensah-Brown, *Ann N. Y. Acad. Sci.* 1084, 49-57 (2006). Related research has demonstrated that reduction in galectin-3 levels slows the breakdown of the inner blood-retinal barrier (iBRB) that typically occurs early in diabetes. Galectin-3 deficient mice demonstrated a significant reduction in diabetes-mediated iBRB and reduced junctional disruption when compared with mice with normal galectin-3 levels. Canning et al, *Exp. Diabetes Res.,* 2007: 51837 (2007). Among the methods available to effectively reduce active galectin-3 concentrations to inhibit the development and progression of diabetes and its symptoms is the administration of low molecular weight MCP over a long term. No toxicity has been demonstrated for such administration.

Arthritis And Inflammation

A model of arthritis may be induced in mice by immunization with methylated bovine serum albumin. Referred to as AIA, this condition mimics arthritis and the inflammation associated with it. Inflammation was shown to be markedly reduced, together with a reduction in bone erosion, in mice with reduced galectin-3 levels. The reduction in arthritis was accompanied by decreased levels of proinflammatory cytokines. Confirming that the nature or the galectin-3 level alteration can be genetic or chemical, exogenously added galectin-3 restored the level of arthritis in galectin-3 deficient mice to wild-type levels. Forsman et al, *Arthritis Rheum.,* 63, 2, 445-54 (2011). Reduction in galectin-3 levels as a means of addressing arthritis and related inflammation was also shown in rats where an artificial reduction in galectin-3 levels via genetic modification substantially suppressed arthritis indices. Wang et al, *Gene Ther.,* 17. 10. 1225-33 (2010). Administering low molecular weight MCP provides an effective in vivo method of achieving this reduction of inflammation and treating arthritis, including autoimmune arthritis such as rheumatoid arthritis.

Skin Inflammation

The development of inflammation in connection with allergic responses presents a vast panorama of patient discomfort. A reduction in galectin-3 levels in galectin-3 deficient mice was shown to reduce epidermal thickening, lower eosinophil infiltration and significantly reduced dermatitis. Saegusa et al., *Am. J. Pathol.,* 174, 3, 922-31 (2009). Inflammation in a wide variety of tissues, as described above, is mediated by galectin-3, at least in part. Reducing the level of active galectin-3 by administration of MCP of molecular weight below 20,000 Daltons down to 10,000 Daltons or lower, and preferably about 3-13,000 Daltons, provides an effective, easily tolerated method of reducing galectin-3 levels to achieve this goal. MCP can also be applied trans-dermally for such purposes.

Cardiac Disease and Fibrosis

As noted, MCP mediated reduction of galectin-3 levels may provide an important treatment for cardiac diseases, particularly by reducing cardiac fibrosis. Reducing galectin-3 levels in the myocardium in osteopontin-deficient mice resulted in diminished fibrotic response and inflammation. Psarras et al, *Eur. Heart. J. April* 2011. Galectin-3 levels associated with mediated fibrosis are much higher than post-fibrotic recovery values. De Boer et al, *Eur. J. Heart Fail.,* 11, 9, 811-17 (2009) suggesting that lowering galectin-3 levels temporarily following heart insult may reduce or suppress fibrosis and heart disease and failure associated therewith.

What has been clearly demonstrated is that reducing galectins-3 levels in serum, cell and particularly in circulation may beneficially affect tissues and organs in mammals. It may also confer protection in mammalian patients presented with challenge from cancer cells, or cells that may develop into cancerous cells. Galectin-3 is a powerful mediator of the development of inflammation and fibrosis and diseases and conditions associated therewith in a wide variety of tissue types, from cardiac to kidney to liver, to lung, to skin. Further, administration of MCP to a mammal in amounts of from 5 mg/kg/day on up to 1,500 mg/kg/day may be effective in reducing and controlling inflammation throughout the body.

While the present invention has been disclosed both generically and with reference to specific alternatives, those alternatives are not intended to be limiting unless reflected in the claims set forth below. The invention is limited only by the provisions of those claims, and their equivalents, as would be recognized by one of skill in the art to which this application is directed, in general, a medical doctor of at least five (5) years experience.

What is claimed is:

1. A method of treating a mammal which benefits from a reduction in available circulating galectin-3, comprising the steps of:
    a) Selecting a mammal in need of at least one of inhibition or reduction of inflammation, and
    b) Administering to said mammal an amount of modified citrus pectin of molecular weight of 3,000-13,000 Daltons, in an amount of 10-750 mg/kg/day, for a period of time sufficient such that said mammal exhibits a reduction in active galectin-3 levels in said mammal and thereby inhibit in said mammal said inflammation or thereby reduce it.

2. A method of treating a mammal which benefits from a reduction in available galectin-3, comprising the steps of:
    a) Selecting a mammal in need of at least one of inhibition and reduction of inflammation, and
    b) administering to said mammal an amount of modified citrus pectin of low molecular weight of 10,000-20,000 Daltons, in an amount of 5-1,500 mg/kg/day, for a period of time sufficient for said mammal to exhibit a reduction in active galectin-3 levels in said mammal and thereby inhibit in said mammal said inflammation or thereby reduce it.

* * * * *